United States Patent [19]

Petitpierre

[11] 4,316,036
[45] Feb. 16, 1982

[54] BENZOPYRANOTHIAZOLES

[75] Inventor: Jean C. Petitpierre, Kaiseraugst, Switzerland

[73] Assignee: Ciba-Geigy Corporation, Ardsley, N.Y.

[21] Appl. No.: 941,432

[22] Filed: Sep. 11, 1978

[30] Foreign Application Priority Data

Sep. 19, 1977 [CH] Switzerland .......................... 11405

[51] Int. Cl.³ .......................................... C07D 277/60
[52] U.S. Cl. .................................... 548/153; 544/111;
544/368; 544/61; 544/60; 544/78; 544/80;
544/82; 546/198; 430/964; 427/151; 282/27.5
[58] Field of Search ...................... 260/306.8 F, 302 F;
544/111, 368, 61, 60, 78, 80, 82; 546/198;
548/153

[56] References Cited

U.S. PATENT DOCUMENTS 2,886,565  5/1959  Prager et al. ..................... 548/153
3,726,891  4/1973  Pilgrim et al. ................ 260/306.8 F
4,033,977  7/1977  Philipp et al. ..................... 548/153

Primary Examiner—Nicholas S. Rizzo
Attorney, Agent, or Firm—John P. Spitals

[57] ABSTRACT

A benzopyranothiazole of the formula

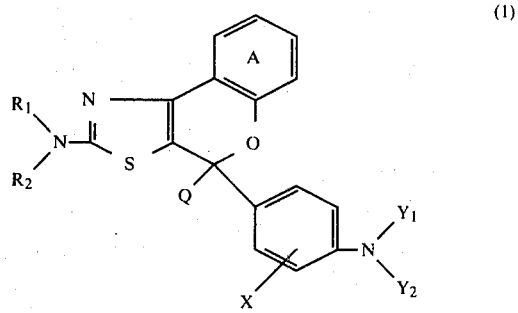

(1)

wherein each of $R_1$ and $R_2$ independently represents hydrogen, alkyl of not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $R_1$ and $R_2$ together with the nitrogen atom to which they are attached represent a 5- or 6-membered heterocyclic radical or a N-carbazolyl radical, Q represents hydrogen, lower alkyl, benzyl or groups of the formulae (1a) or (1b)

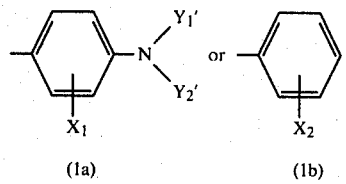

(1a)        (1b)

each of X, $X_1$ and $X_2$ represents hydrogen, halogen, lower alkyl or lower alkoxy, each of $Y_1$, $Y_2$, $Y'_1$ and $Y'_2$ represents hydrogen, alkyl of not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or each of the pair of substituents $Y_1$ and $Y_2$ and $Y'_1$ and $Y'_2$, together with the nitrogen atom to said pair is attached, independently represents a 5- or 6-membered heterocyclic radical or a N-carbazolyl radical and the ring A is unsubstituted or substituted by halogen, nitro, lower alkyl, lower alkoxy, phenoxy or an amino group which is unsubstituted or substituted by lower alkyl, phenyl or benzyl; these compounds are particularly useful as color formers which give intense red to blue color shades of excellent light fastness when they are brought into contact with an electron-accepting co-reactant.

5 Claims, No Drawings

BENZOPYRANOTHIAZOLES

The present invention relates to benzopyranothiazoles, a process for their production, and their use as colour formers in pressure-sensitive or heat-sensitive recording material.

The novel benzopyranothiazoles have the formula

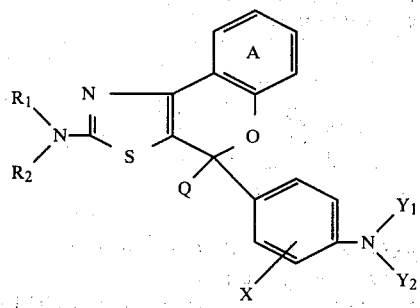
(1)

wherein each of $R_1$ and $R_2$ independently represents hydrogen, alkyl of not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $R_1$ and $R_2$ together with the nitrogen atom to which they are attached represent a 5- or 6-membered heterocyclic radical or a N-carbazolyl radical, Q represents hydrogen, lower alkyl, benzyl or a group of the formula (1a) or (1b)

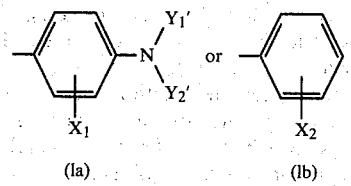

(1a) (1b)

each of X, $X_1$ and $X_2$ represents hydrogen, halogen, lower alkyl or lower alkoxy, each of $Y_1$, $Y_2$, $Y'_1$ and $Y'_2$ represents hydrogen, alkyl of not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or each of the pair of substituents $Y_1$ and $Y_2$ and $Y'_1$ and $Y'_2$, together with the nitrogen atom to which said pair is attached, independently represents a 5- or 6-membered heterocyclic radical or a N-carbazolyl radical and the ring A is unsubstituted or substituted by halogen, nitro, lower alkyl, lower alkoxy, phenoxy or an amino group which is unsubstituted or substituted by lower alkyl, phenyl or benzyl.

In the definition of the radicals of the benzopyranothiazoles, lower alkyl or lower alkoxy denotes as a rule those groups which contain 1 to 5, in particular 1 to 3, carbon atoms, for example methyl, ethyl, n-propyl, isopropyl, n-butyl, sec-butyl or amyl, and methoxy, ethoxy or isopropoxy.

Alkyl groups represented by $R_1$, $R_2$, $Y_1$, $Y_2$, $Y'_1$ and $Y'_2$ can be straight chain or branched. Examples of such alkyl radicals are methyl, ethyl, n-propyl, isopropyl, n-butyl, sec-butyl, n-hexyl, n-octyl or n-dodecyl.

Substituted alkyl radicals $R_1$, $R_2$, $Y_1$, $Y_2$, $Y'_1$ and $Y'_2$ are in particular cyanoalkyl, haloalkyl, hydroxyalkyl, alkoxyalkyl, each containing preferably altogether 2 to 4 carbon atoms, for example β-cyanoethyl, β-chloroethyl, β-hydroxyethyl, β-methoxyethyl or β-ethoxyethyl.

R and Y as cycloalkyl are for example cyclopentyl or preferably cyclohexyl.

Preferred substituents in the benzyl and phenyl group of the R and Y radicals are for example halogen atoms, methyl or methoxy. Examples of such araliphatic and aromatic radicals are: p-methylbenzyl, o- or p-chlorobenzyl, o- or p-tolyl, xylyl, o-, m- or o-chlorobenzyl or o- or p-methoxyphenyl.

If each of the pair of substituents $R_1$ and $R_2$, $Y_1$ and $Y_2$ and $Y'_1$ and $Y'_2$, together with the nitrogen atom to which they are attached, represents a heterocyclic radical, such a radical is for example pyrrolidino, piperidino, pipecolino, morpholino, thiomorpholino or piperazino.

The substituents $R_1$ and $R_2$ are preferably benzyl or lower alkyl.

The radical Q is advantageously the group of the formula (1a). X, $X_1$ and $X_2$ are preferably hydrogen or also halogen, methyl, methoxy or ethoxy.

The ring A is preferably not further substituted or it is further substituted by halogen, lower alkyl or lower alkoxy, for example by chlorine, methyl, tert-butyl or methoxy.

Halogen in connection with the above substituents of the formula (1) is for example fluorine, bromine or preferably chlorine.

Colour formers of the formula (1) having an interesting utility are those of the formula

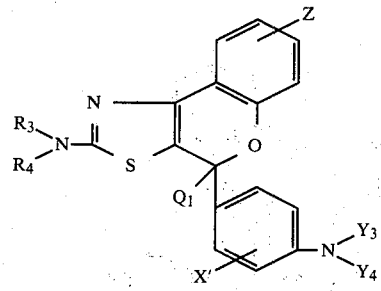
(2)

wherein $R_3$, $R_4$, $Y_3$ and $Y_4$, each independently of the other, represent lower alkyl, phenyl or benzyl and $R_3$ also represents hydrogen, or each of the pair of substituents $R_3$ and $R_4$ and $Y_3$ and $Y_4$, together with the nitrogen atom to which said pair is attached, independently represents a pyrrolidino, piperidino, morpholino or carbazolyl radical, $Q_1$ represents hydrogen, lower alkyl, phenyl, benzyl or the group of the formula

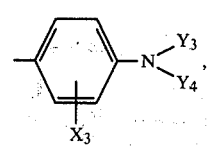
(2a)

each of X' and $X_3$ represents hydrogen, halogen, methyl or lower alkoxy and Z represents hydrogen, halogen, lower alkyl, lower alkoxy or an amino group which is unsubstituted or substituted by lower alkyl, benzyl or phenyl.

Particularly interesting benzopyranothiazoles are those of the formula

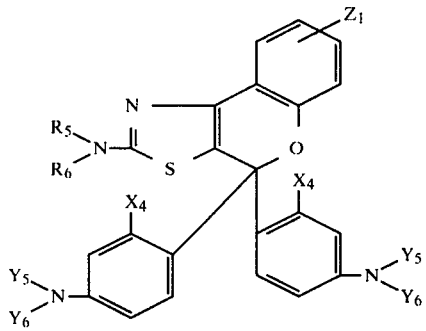 (3)

wherein each of $R_5$ and $R_6$ represents lower alkyl, benzyl or phenyl, or together with the nitrogen atom to which they are attached represent a N-carbazolyl radical, each of $Y_5$ und $Y_6$ represents lower alkyl or benzyl, $X_4$ represents hydrogen, methyl, methoxy or ethoxy, and $Z_1$ represents hydrogen, chlorine, methyl, methoxy or an amino group which is mono- or disubstituted by lower alkyl.

Especially preferred benzopyranothiazoles of the formula (3) are those wherein $R_5$ and $R_6$ represent lower alkyl or benzyl.

The most preferred benzopyranothiazoles are those of the formula

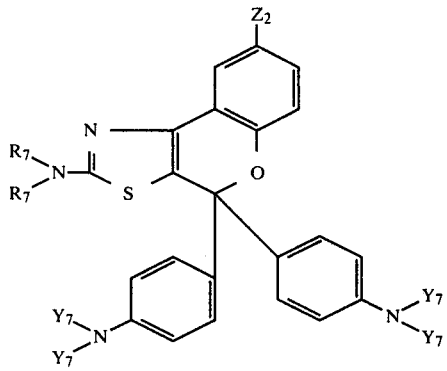 (4)

wherein each of $R_7$ and $Y_7$ represents methyl or ethyl and $Z_2$ represents hydrogen or methyl.

The benzopyranothiazoles of the formulae (1) to (4) are obtained by reacting a compound of the formula

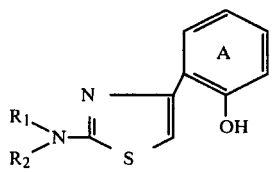 (5)

with a compound of the formula

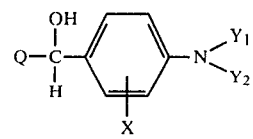 (6)

and subsequently oxidising the reaction product, or by reacting the compound of the formula (5) with a keto compound of the formula

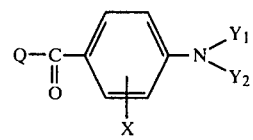 (7)

In the formulae (5), (6) und (7) above, A, $R_1$, $R_2$, Q, X, $Y_1$ and $Y_2$ have the given meanings.

The reaction with the keto compound of the formula (7) is preferably carried out by reacting the reactants in the presence of an acid condensation agent. Examples of such condensation agents are sulfuric acid, oleum, phosphorus pentoxide or preferably acid halides.

Suitable acid halides are acid bromides or preferably acid chlorides of phosphorous or sulfurous acid, of phosphoric acid, sulfuric acid, carbonic acid or oxalic acid. Oxalyl chloride, oxalyl bromide, thionyl chloride, sulfuryl chloride, phosphorus trichloride, phosphorus tribromide or preferably phosgene, or most preferably phosphorus oxychloride, are used with advantage.

The reaction of the compound of the formula (5) with the keto compound (7) can be carried out at a temperature between 20° and 120° C., advantageously under anhydrous conditions. An excess of the acid halide can be used as reaction medium; but an inert solvent can also be added under the reaction conditions.

Examples of suitable solvents are: cycloaliphatic or aromatic hydrocarbons, for example cyclohexane, benzene, toluene or xylenes; chlorinated hydrocarbons, such as chloroform, carbon tetrachloride, ethylene chloride or chlorobenzenes; ethers, such as dioxan, diethyl ether, glycol dimethyl ether or tetrahydrofurane.

The concentration of the reactants is not critical; however, it is advantageous to use one molar equivalent of each of the reaction components. The process is normally carried out such that all reactants, i.e. the compound of the formula (5), the compound of the formula (7), and the acid halide, are reacted simultaneously. However, the procedure can also be that the compound of the formula (5) is reacted first with the acid halide and then the compound of the formula (7) is added. The end product of the formula (1) is isolated in a manner which is known per se, for example by pouring the reaction mixture into ice-water, if desired while neutralising the acids with an alkaline compound, for example with an alkali metal hydroxide or alkali metal carbonate, collecting the precipitate by filtration and washing and drying it, and also by chromatography or recrystallisation of the product. Liquid end products can be obtained by extraction with suitable organic solvents and, if desired, by distillation.

The condensation of the compounds of the formulae (5) and (6) is advantageously carried out in an organic solvent, especially in a lower aliphatic alcohol, for example methanol, ethanol or isopropanol, or in an ether, for example tetrahydrofurane, and preferably in the presence of an acid catalyst. The reaction can be carried out at room temperature (20° to 25° C.). However, it is advantageous to carry out the reaction at elevated temperature, preferably from 40° to 100° C. Suitable acid catalysts are for example lower aliphatic carboxylic acids, such as formic acid or acetic acid, and inorganic acids, such as hydrochloric acid, sulfuric acid, phosphoric acid or perchloric acid. The reaction time depends on the temperature and is normally from half an hour to 15 hours.

The reaction of the compound of the formula (5) with the compound of the formula (6) yields a reaction product of the formula

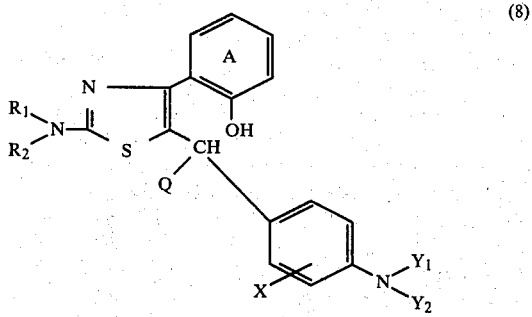

(8)

wherein $R_1$, $R_2$, $Y_1$, $Y_2$, A, Z and Q have the given meanings, with the elimination of water.

If desired, the reaction product of the formula (8) can be isolated.

The oxidation of the reaction products of the formula (8) to give the benzopyranothiazoles of the formula (1) is effected with oxidising agents. Examples of suitable oxidising agents are: chromates, bichromates, chlorates, chlorites, peroxides, manganese dioxide, lead dioxide, chlorine, bromine, molecular oxygen, air, perborates, permanganates, hydrogen peroxide and, especially, chloranil.

The process is advantageously carried out in the presence of an organic solvent which does not participate in the oxidation. Suitable solvents are once more lower aliphatic alcohols, such as ethanol, isopropanol, ethylene glycol monomethyl ether or ethylene glycol monoethyl ether, or lower aliphatic ketones, such as acetone, methyl ethyl ketone or methyl isobutyl ketone, or aromatic hydrocarbons, such as benzene or toluene.

The best results as regards the yield and purity of the benzopyranothiazoles of the present invention are obtained with chloranil as preferred oxidising agent, preferably in toluene.

The oxidation temperature depends normally on the oxidising agent and, in particular, on the boiling point of the solvent employed. It is desirably between 20° and 150° C., preferably between 20° and 100° C. When using chloranil, the oxidation takes place preferably at room temperature. The oxidation normally takes from 5 to 30 hours.

The benzopyranothiazoles of the formulae (1) to (4) are normally colourless or faintly coloured. When these colour formers are brought into contact with an acid developer, i.e. an electron acceptor, they produce intense red to blue shades of excellent lightfastness. They are therefore also very useful when mixed with other known colour formers, for example 3,3-(bis-aminophenyl)-phthalides, 3,3-(bis-indolyl)-phthalides, 2,6-diaminofluoranes, spiropyranes or benzoyl leucomethylene blue in order to give blue, navy blue, grey or black colouration.

The benzopyranothiazoles of the formulae (1) to (4) exhibit both on clay and on phenolic substrates an improved colour intensity and lightfastness. They are suitable in particular as instant developing colour formers for use in a pressure-sensitive or heat-sensitive recording material, which can be copying material and also documenting material.

A pressure-sensitive material consists for example of at least one pair of sheets, which contain at least one colour former of the formulae (1) to (4), dissolved in an organic solvent, and a solid electron acceptor as developer. The colour former effects a coloured marking at those points where it comes into contact with the electron acceptor. Typical examples of such developers are attapulgite clay, acid-activated bentonite (silton clay), silica, bentonite, montmorillonite, halloysite, aluminium oxide, aluminium sulphate, aluminium phosphate, zinc chloride, kaolin or any acid clay or organic compounds with acid reaction, for example unsubstituted or ring-substituted phenols, salicylic acid or esters of salicyclic acid and the metal salts thereof, or an acid polymeric material, for example a phenolic polymer, an alkylphenolacetylene resin, a maleic acid/colophonium resin or a partially or completely hydrolysed polymer of maleic acid and styrene, ethylene, vinyl methyl ether or carboxypolymethylene. Preferred developers are attapulgite clay, silton clay or phenolformaldehyde resin. These electron acceptors are preferably applied in the form of a layer to the face of the receiver sheet.

In order to prevent the colour formers contained in the pressure-sensitive recording material from becoming prematurely active, they are usually separated from the electron acceptor. This can advantageously be accomplished by incorporating the colour formers in foam-like, sponge-like or honeycomb-like structures. Preferably, however, the colour formers are enclosed in microcapsules, which usually can be ruptured by pressure.

When the capsules are ruptured by pressure, for example with a pencil, and the colour former solution is transferred to an adjacent sheet which is coated with an electron acceptor, a coloured area is formed. This colour is produced by the resulting dye, which is absorbed in the visible range of the electromagnetic spectrum.

The colour formers are encapsulated preferably in the form of solutions in organic solvents. Examples of suitable solvents are preferably non-volatile solvents, for example polyhalogenated paraffin or diphenyl, such as trichlorodiphenyl or a mixture thereof with liquid paraffin; tricresyl phosphate, di-n-butyl phthalate, dioctyl phthalate, trichlorobenzene, nitrobenzene, trichloroethyl phosphate hydrocarbon oils, such as paraffin, alkylated derivatives of naphthalene or diphenyl, terphenyls, partially hydrogenated terphenyl, or other chlorinated or hydrogenated condensed aromatic hydrocarbons.

The capsule walls can be formed evenly around the droplets of the colour former solution by coacervation, and the encapsulating material can consist of gelatin and gum arabic, as described e.g. in U.S. Pat. No. 2,800,457. The capsules can also be formed preferably from an aminoplast or from modified aminoplasts by polycondensation, as described in British Pat. Nos. 989 264, 1 156 725, 1 301 052 and 1 355 124.

The microcapsules containing the colour formers of formula (1) can be used for the production of a wide variety of known kinds of pressure-sensitive copying material. The various systems differ substantially from one another in the arrangement of the capsules, the colour reactants and the carrier material.

A preferred arrangement is that in which the encapsulated colour former is applied as a layer to the back of a transfer sheet and the electron acceptor substance as a layer to the face of a receiver sheet. However the components can also be used in the paper pulp.

Another arrangement of the constituents consists in the microcapsules which contain the colour former, and the developer, being in or on the same sheet, in the form of one or more individual sheets or being present in the paper pulp.

Such pressure-sensitive copying materials are described, for example, in U.S. Pat. Nos. 2,730,457, 2,932,582, 3,418,250, 3,427,180 and 3,516,846. Further systems are described in British Pat. Nos. 1,042,596, 1,042,597, 1,042,598, 1,042,599, and 1,053,935. Microcapsules which contain the colour formers of formula (1) are suitable for each of these systems and for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

The term "paper" used herein comprises not only normal paper made from cellulose fibres, but also paper in which the cellulose fibres are replaced (partially or completely) by synthetic polymer fibres.

The benzopyranothiazoles of the formulae (1) to (4) can also be used as colour formers in a thermoreactive recording material. This recording material contains normally at least one carrier, one colour former, a solid electron acceptor and optionally also a binder. Thermoreactive recording systems comprise for example heat sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in the binder in one paper. By means of heat the binder is softened at specific areas and the colour former comes into contact with the electron acceptor at those points where heat is applied and the desired colour develops at once.

The developers are the same electron-accepting substances as are used in pressure-sensitive papers. Examples of developers are the acid clays and phenolic resins already mentioned, or also phenolic compounds, for example 4-tert-butylphenol, 4-phenylphenol, 4-hydroxydiphenyl oxide, α-naphthol, β-naphthol, 4-hydroxymethyl benzoate, 4-hydroxyacetophenone, 2,2'-dihydroxydiphenyl, 4,4-isopropylidene-diphenol, 4,4'-isopropylidene-bis-(2-methylphenyl), 4,4'-bis-(hydroxyphenyl)valeric acid, hydroquinone, pyrogallol, chloroglucinol, p-, m- and o-hydroxybenzoic acid, gallic acid, 1-hydroxy-2-naphthoic acid, as well as boric acid and aliphatic dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the colour formers and the developer are insoluble in water. The binder should be able to disperse and fix the colour former and the developer at room temperature.

By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. To improve the degree of whiteness, to facilitate the printing of papers, and to prevent the heated pen from sticking, the coating can contain, for example, talc, $TiO_2$, $ZnO$ or $CaCO_3$ or also organic pigments, for example urea/formaldehyde polymers. In order to effect the colour formation only within a limited temperature range, it is possible to add substances such as urea, thiourea, acetanilide, phthalic anhydride or other appropriate fusible products which induce the simultaneous melting of the colour former and developer.

In the following Examples, the percentages are by weight unless otherwise indicated.

EXAMPLE 1

17.5 g or 2-chloroacetyl-4-methylphenol and 10.9 g of N,N-dimethyl thiourea are heated for 20 minutes to 110° C. After cooling, the solidified mass is recrystallised from aqueous methanol, affording 14.2 g (96% of theory) of 2-dimethylamino-4-(2'-hydroxy-5'-methylphenyl)-thiazole of the formula (101)

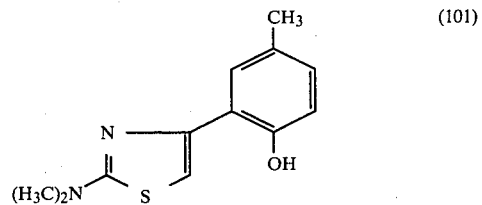

with a melting point of 108°–110° C.

A mixture of 5.4 g of 4,4'-bis-(dimethylamino)-benzhydrol ("Michler's hydrol"), 4.9 g of the compound of the formula (101), 60 ml of ethanol and 1 ml of glacial acetic acid are refluxed for 18 hours. The mixture is cooled to room temperature, the precipitate is collected by filtration and washed with a small amount of methanol, affording 6.1 g (63% of theory) of 2-dimethylamino-4-(2'-hydroxy-5'-methylphenyl)-5-[bis-(4"-dimethylaminophenyl)-methyl]-thiazole of the formula

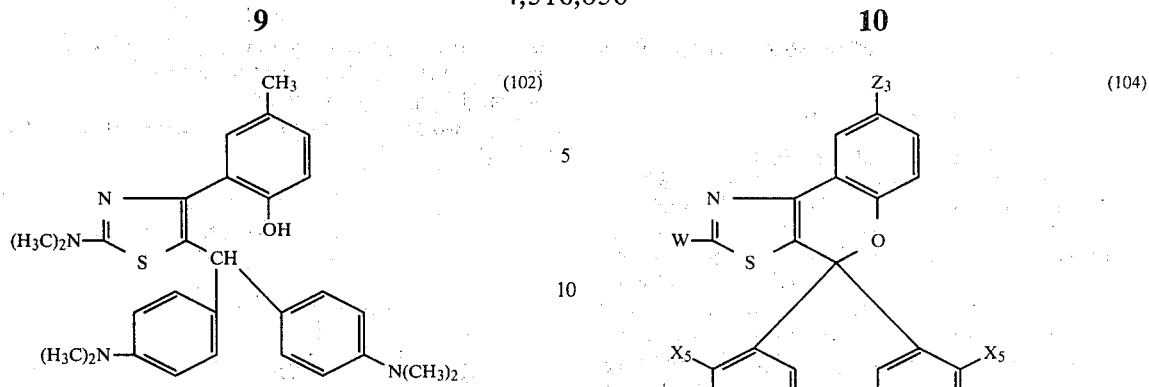

with a melting point of 189°–191° C.

A mixture of 4.86 g of the compound of the formula (102), 2.52 g of chloroanil and 60 ml of toluene is stirred for 20 hours at room temperature. The resulting precipitate is collected by filtration and washed with 10 ml of toluene, affording 3.1 g (64% of theory) of a benzopyranothiazole compound of the formula (103) with a melting point of 227°–229° C. This colour former develops on silton clay a blue colour with λmax. at 648 nm.

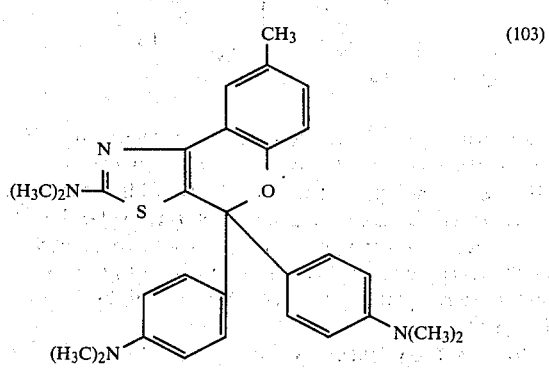

The colour formers of the formula listed in the following table are obtained in the same manner as described in Example 1.

TABLE

| Example | W | $Z_3$ | T | $X_5$ | Colour on silton-clay |
|---|---|---|---|---|---|
| 2 | —N($C_2H_5$)$_2$ | H | —N($CH_3$)$_2$ | H | blue |
| 3 | —N($C_2H_5$)$_2$ | $CH_3$ | —N($CH_3$)$_2$ | H | blue |
| 4 | —N($C_2H_5$)$_2$ | $CH_3$ | —N($CH_3$)$_2$ | H | blue |
| 5 | —N($CH_3$)$_2$ | Cl | —N($C_2H_5$)$_2$ | H | blue |
| 6 | —N($CH_2$—Ph)$_2$ | $CH_3$ | —N($C_2H_5$)$_2$ | H | blue |
| 7 | —N($CH_3$)$_2$ | —O$CH_3$ | —N($CH_3$)$_2$ | H | blue |
| 8 | —N(Ph)CH$_3$ | | | | |
| 9 | —N($CH_3$)$_2$ | $CH_3$ | —N($CH_2$—Ph)$_2$ | H | blue |
| 10 | —N($CH_3$)$_2$ | $CH_3$ | —N($C_2H_5$)$_2$ | —O$CH_3$ | blue |
| 11 | —N($CH_3$)$_2$ | —N($CH_3$)$_2$ | —N($C_2H_5$)$_2$ | H | blue |
| 12 | —N(pyrrolidinyl) | $CH_3$ | —N($C_2H_5$)$_2$ | H | blue |
| 13 | —N($CH_3$)$_2$ | $CH_3$ | —N(piperidinyl) | H | blue |
| 14 | —N($CH_3$)$_2$ | $CH_3$ | —N($C_2H_5$)$_2$ | —O$C_2H_5$ | blue |

EXAMPLE 15

Production of a pressure-sensitive copying paper

A solution of 3 g of the benzopyranothiazole of the formula (103) in 97 g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resulting emulsion is poured into 600 g of ice-water and cooled, whereupon the coacervation is effected. A sheet of paper is coated with the resulting suspension of microcapsules and dried. A second sheet of paper is then coated with silton clay. The first sheet and the sheet of paper coated with silton clay are laid on top of each other with the coated sides face to face. Pressure is exerted on the first sheet by writing by hand or with a typewriter and an intense blue copy of excellent light-fastness instantly develops on the sheet coated with silton clay. Corresponding intense blue copies are also obtained using each of the other colour formers of Examples 2 to 14.

EXAMPLE 16

Production of a thermoreactive paper 6 g of an aqueous dispersion which contains 1.57% of the benzopyranothiazole of the formula (103) and 6.7% of polyvinyl alcohol are mixed with 134 g of an aqueous dispersion which contains 14% of 4,4-isopropylidene-diphenol, 8% of attapulgite clay and 6% of polyvinyl alcohol. This mixture is applied to a paper and dried. Contacting the paper with a heated ball-point pen produces an intense blue colour of excellent lightfastness.

Intense blue colours can also be obtained by using each of the other colour formers of the Examples (2) to (14)

What is claimed is:

1. A benzopyranothiazole of the formula

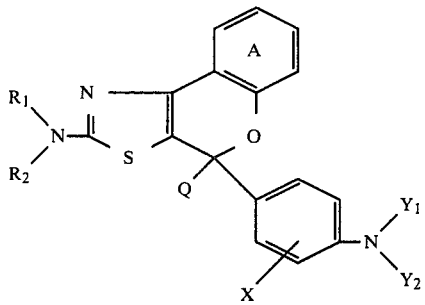
(1)

wherein each of $R_1$ and $R_2$ independently represents hydrogen, alkyl of not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $R_1$ and $R_2$ together with the nitrogen atom to which they are attached represents a 5- or 6-membered heterocyclic radical selected from the group consisting of pyrrolidino, piperidino, pipecolino, morpholino, thiomorpholino or piperazino, or a N-substituted carbazole, Q represents hydrogen, lower alkyl, benzyl or groups of the formulae (1a) or (1b)

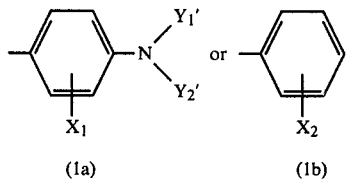

(1a)    (1b)

each of X, $X_1$ and $X_2$ represents hydrogen, halogen, lower alkyl or lower alkoxy, each of $Y_1$, $Y_2$, $Y_1$ and $Y_2$ represents hydrogen, alkyl of not more than 12 carbon atoms which is unsubstituted or substituted by halogen, hydroxyl cyano or lower alkoxy, or represents cycloalkyl, phenyl, benzyl, or phenyl or benzyl which is substituted by halogen, lower alkyl or lower alkoxy, or each of the pair of substituents $Y_1$ and $Y_2$ and $Y_1$ and $Y_2$, together with the nitrogen atom to said pair is attached, independently represednt a 5- or 6-membered heterocyclic radical selected from the group consisting of pyrrolidino, piperidino, pipecolino, morpholino, thiomorpholino or piperazino, or a N-unsubstituted carbazole and the ring A is unsubstituted or substituted by halogen, nitro, lower alkyl, lower alkoxy, phenoxy or an amino group which is unsubstituted or substituted by lower alkyl, phenyl or benzyl.

2. A benzopyranothiazole according to claim 1 of the formula

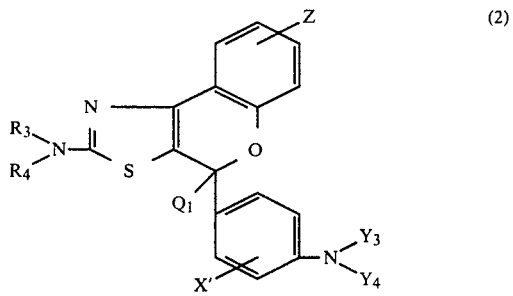
(2)

wherein $R_3$, $R_4$, $Y_3$ and $Y_4$, each independently of the other, represent lower alkyl, phenyl or benzyl and $R_3$ also represents hydrogen, or each of the pair of substituents $R_3$ and $R_4$ and $Y_3$ and $Y_4$, together with the nitrogen atom to which said pair is attached, independently represents a pyrrolidino, piperidino, morpholino or unsubstituted carbazole, $Q_1$ represents hydrogen, lower alkyl, phenyl, benzyl or the group of the formula

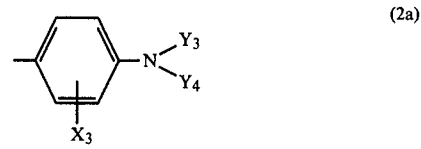
(2a)

each of X' and $X_3$ represents hydrogen, halogen, methyl or lower alkoxy and Z represents hydrogen, halogen, lower alkyl, lower alkoxy or an amino group which is unsubstituted or substituted by lower alkyl, benzyl or phenyl.

3. A benzopyranothiazole according to claim 2 of the formula

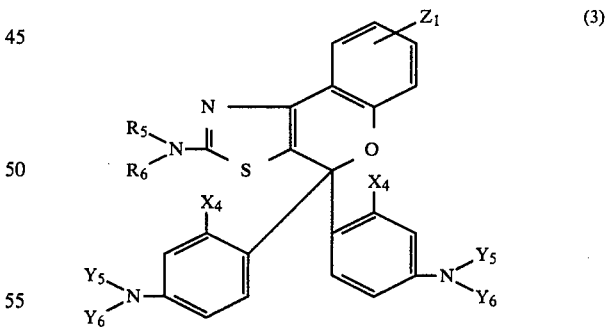
(3)

wherein each of $R_5$ and $R_6$ represents lower alkyl, benzyl or phenyl, or together with the nitrogen to which they are attached represent a N-unsubstituted carbazole, each of $Y_5$ and $Y_6$ represents lower alkyl or benzyl, $X_4$ represents hydrogen, methyl, methoxy or ethoxy, and $Z_1$ represents hydrogen, chlorine, methyl, methoxy or an amino group which is mono- or disubstituted by lower alkyl.

4. A benzopyranothiazole according to claim 3 of the formula (3), wherein $R_5$ and $R_6$ represent lower alkyl or benzyl.

5. A benzopyranothiazole according to claim 3 of the formula
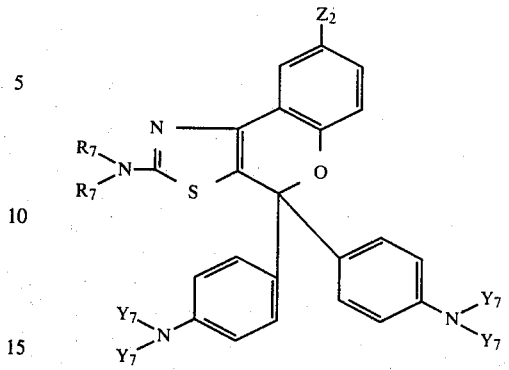
wherein each of $R_7$ and $Y_7$ represents methyl or ethyl and $Z_2$ represents hydrogen or methyl.
* * * * *